United States Patent [19]
Gasper et al.

[11] Patent Number: 6,080,779
[45] Date of Patent: *Jun. 27, 2000

[54] COMPOSITIONS AND METHODS FOR STIMULATING BONE GROWTH

[75] Inventors: Shirley R. Gasper; Robert R. West, both of Seattle; Theresa Martinez, Greenbank; Kirk G. Robbins, Renton; Patricia A. McKernan, Woodinville; Nand Baindur, Edmonds, all of Wash.; Virender M. Labroo, Banglore, India; Gregory R. Mundy, San Antonio, Tex.

[73] Assignees: OsteoScreen, Inc., San Antonio, Tex.; ZymoGenetics Corporation, Seattle, Wash.

[*] Notice: This patent is subject to a terminal disclaimer.

[21] Appl. No.: 09/096,957

[22] Filed: Jun. 12, 1998

Related U.S. Application Data

[63] Continuation-in-part of application No. 08/989,862, Dec. 12, 1997.
[60] Provisional application No. 60/032,893, Dec. 13, 1996.

[51] Int. Cl.[7] .................. A61K 31/335; A61K 31/33; A61K 31/66
[52] U.S. Cl. ................ 514/451; 514/141; 514/185; 514/700
[58] Field of Search ................... 514/451, 185, 514/141, 700

[56] References Cited

U.S. PATENT DOCUMENTS

| | | | |
|---|---|---|---|
| 5,258,376 | 11/1993 | Bernstein .................. | 514/184 |
| 5,280,040 | 1/1994 | Labroo et al. .............. | 514/422 |
| 5,462,932 | 10/1995 | Brenner et al. ............. | 514/108 |
| 5,545,661 | 8/1996 | Cullinan .................... | 514/460 |
| 5,604,257 | 2/1997 | Tabe et al. ................. | 514/460 |

FOREIGN PATENT DOCUMENTS

| | | | |
|---|---|---|---|
| WO 97/15308 | 5/1997 | WIPO ................. | A61K 31/54 |

OTHER PUBLICATIONS

Wozney, J.M., "The Bone Morphogenetic Protein Family and Osteogenesis," *Molecular Reproduction and Development* 32:160–167 (Jun. 1992).

Harris, S.E., et al., "Effects of Transforming Growth Factor β on Bone Nodule Formation and Expression of Bone Morphogenetic Protein 2, Osteocalcin, Osteopontin, Alkaline Phosphatase, and Type I Collagen mRNA in Long–Term Cultures of Fetal Rat Calvarial Osteoblasts," *Journal of Bone Mineral Research* 9(6):855–863 (Jun. 1994).

Luckman, S.P. et al. , J.Bone Min Res (1998) 13:581–589.

Wang, G–J., et al., "Lipid Clearing Agents in Steroid–induced Osteoporosis," *J Formos Med Assoc* 94(10):589–592 (Oct. 1995).

Cui, Q., et al., "Lovastatin Prevents Steroid–Induced Adipogenesis and Osteoporosis," Reports of the ASBMR 18th Annual Meeting (Sep. 1996) *Journal of Bone and Mineral Research* (Aug. 1996) 11(Supplement 1):S510, p. S217.

Bellows, C.G., et al., "Determination of the Capacity for Proliferation and Differentiation of Osteoprogenitor Cells in the Presence and Absence of Dexamethasone," *Developmental Biology* 140:132–138 (Jul. 1990).

Rickard, D.J. et al., "Induction of Rapid Osteoblast Differentiation in Rat Bone Marrow Stromal Cell Cultures by Dexamethasone and BMP–2," *Developmental Biology* (1994) 161:218–228.

Ducy, P., et al., "Increased bone formation in osteocalcin–deficient mice,"*Nature* (Aug. 1, 1996) 382:448–452.

*Primary Examiner*—Ralph Gitomer
*Assistant Examiner*—Marjorie A. Moran
*Attorney, Agent, or Firm*—Morrison & Foerster LLP

[57] ABSTRACT

Compounds of the formula

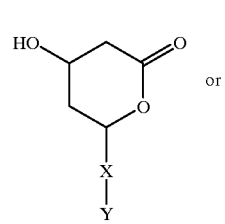

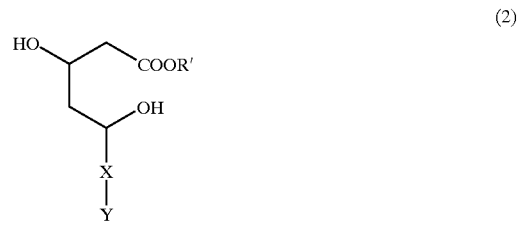

wherein X in each of formulas (1) and (2) represents a substituted or unsubstituted alkylene, alkenylene, or alkynylene linker of 2–6 C;

Y represents one or more carbocyclic or heterocyclic rings; when two or more rings are present in Y, they may optionally be fused; and R' represents a cation, H or a substituted or unsubstituted alkyl group of 1–6 C; and the dotted lines represent optional π-bonds, promote bone formation and are thus useful in treating osteoporosis, bone fracture or deficiency, primary or secondary hyperparathyroidism, periodontal disease or defect, metastatic bone disease, osteolytic bone disease, post-plastic surgery, post-prosthetic joint surgery, and post-dental implantation. These compounds can be used in combination with other bone growth-promoting compounds and/or estrogens and/or bisphosphonates for this purpose.

20 Claims, 1 Drawing Sheet

R = R' = H   59-0327 Max: 165%; $EC_{50}$:5μM (mevastatin)
R = H; R' = $CH_3$   59-0326 Max: 155%; $EC_{50}$:2.5μM (lovastatin)
R = R' = $CH_3$   59-0328 Max: 150%; $EC_{50}$:1.25μM (simvastatin)

59-0329 (hydrolyzed pravastatin)

59-0342 Max 175%; $EC_{50}$:1.25 uM (fluvastatin)

COMPOSITIONS AND METHODS FOR STIMULATING BONE GROWTH

This application claims priority under 35 USC 119 from provisional application Ser. No. 60/032,893 filed Dec. 13, 1996. It is also a continuation-in-part of U.S. Ser. No. 08/989,862 filed Dec. 12, 1997 claiming benefit under 35 USC 120. The entire contents of these documents are incorporated herein by reference.

TECHNICAL FIELD

The invention relates to compositions and methods for use in limiting the consequences of undesired bone loss in a vertebrate at risk of such bone loss, in treating conditions that are characterized by undesired bone loss or by the need for bone growth, in treating fractures, and in treating cartilage disorders. More specifically, the invention concerns the use of specific classes and combinations of compounds for this purpose.

BACKGROUND ART

Bone is subject to constant breakdown and resynthesis in a complex process mediated by osteoblasts, which produce new bone, and osteoclasts, which destroy bone. The activities of these cells are regulated by a large number of cytokines and growth factors, many of which have now been identified and cloned.

Although there is a great deal of information available on the factors which influence the breakdown and resorption of bone, information on growth factors which stimulate the formation of new bone is more limited. Investigators have searched for sources of such activities, and have found that bone tissue itself provides factors which have the capacity for stimulating bone cells. Thus, extracts of bovine bone tissue obtained from slaughterhouses contain not only structural proteins which are responsible for maintaining the structural integrity of bone, but also biologically active bone growth factors which can stimulate bone cells to proliferate. Among these factors are transforming growth factor β, the heparin-binding growth factors (e.g., acidic and basic fibroblast growth factor), the insulin-like growth factors (e.g., insulin-like growth factor I and insulin-like growth factor II), and a recently described family of proteins called bone morphogenetic proteins (BMPs). All of these growth factors have effects on other types of cells, as well as on bone cells.

The BMPs are novel factors in the extended transforming growth factor β superfamily. Recombinant BMP2 and BMP4 can induce new bone formation when they are injected locally into the subcutaneous tissues of rats (Wozney J. *Molec Reprod Dev* (1992) 32:160–67). These factors are expressed by normal osteoblasts as they differentiate, and have been shown to stimulate osteoblast differentiation and bone nodule formation in vitro as well as bone formation in vivo (Harris S. et al. *J. Bone Miner Res* (1994) 9:855–63). This latter property suggests potential usefulness as therapeutic agents in diseases which result in bone loss.

The cells which are responsible for forming bone are osteoblasts. As osteoblasts differentiate from precursors to mature bone-forming cells, they express and secrete a number of enzymes and structural proteins of the bone matrix, including Type-1 collagen, osteocalcin, osteopontin and alkaline phosphatase. They also synthesize a number of growth regulatory peptides which are stored in the bone matrix, and are presumably responsible for normal bone formation. These growth regulatory peptides include the BMPs (Harris S. et al. (1994), supra). In studies of primary cultures of fetal rat calvarial osteoblasts, BMPs 1, 2, 3, 4, and 6 are expressed by cultured cells prior to the formation of mineralized bone nodules (Harris S. et al. (1994), supra). Like alkaline phosphatase, osteocalcin and osteopontin, the BMPs are expressed by cultured osteoblasts as they proliferate and differentiate.

Although the BMPs are potent stimulators of bone formation in vitro and in vivo, there are disadvantages to their use as therapeutic agents to enhance bone healing. Receptors for the bone morphogenetic proteins have been identified in many tissues, and the BMPs themselves are expressed in a large variety of tissues in specific temporal and spatial patterns. This suggests that BMPs may have effects on many tissues in addition to bone, potentially limiting their usefulness as therapeutic agents when administered systemically. Moreover, since they are peptides, they would have to be administered by injection. These disadvantages impose severe limitations to the development of BMPs as therapeutic agents.

There is a plethora of conditions which are characterized by the need to enhance bone formation. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis.

There are currently no satisfactory pharmaceutical approaches to managing any of these conditions. Bone fractures are still treated exclusively using casts, braces, anchoring devices and other strictly mechanical means. Further bone deterioration associated with post-menopausal osteoporosis has been treated with estrogens or bisphosphonates, which have known side effects when used at levels required when they are administered alone.

U.S. Pat. No. 5,280,040 discloses compounds described as useful in the treatment of osteoporosis. These compounds putatively achieve this result by preventing bone resorption.

Nitrogen-containing bisphosphonates, generally, have been shown to inhibit bone resorption presumably by leading to osteoclast apoptosis. See, for example, Luckman, S. P. et al. *J Bone Min Res* (1998) 13:581–589. The nitrogen-containing bisphosphonates are well known, and they contain phosphonate residues coupled through a carbon rather than through an oxygen moiety. Typical bisphosphonates include alendronate, ibandronate and risedronate.

Wang, G.-J. et al., *J Formos Med Assoc* (1995) 94:589–592 report that certain lipid clearing agents, exemplified by lovastatin and bezafibrate, were able to inhibit the bone resorption resulting from steroid administration in rabbits. There was no effect on bone formation by these two compounds in the absence of steroid treatment. The mechanism of the inhibition in bone resorption observed in the presence of steroids (and the mechanism of the effect of steroid on bone per se) is said to be unknown. The authors state that steroid-induced bone loss is associated with a decrease in bone formation attributed to an inhibitory effect of corticosteroid on osteoblast activity and an increase in bone absorption due to direct osteoclast stimulation and to an indirect inhibition of intestinal calcium absorption with a secondary increase in parathyroid hormone production. Other mechanisms mentioned include those attributable to lipid abnormalities and hyperlipidemia which lead to circulatory impairment, obstruction of subchondral vessels, osteocyte necrosis and osteoporosis. In light of the known activities of lovastatin and bezafibrate, the authors attribute the effect on bone loss to their ability to lower lipid levels and overcome the impairment to circulation within the femoral head. There is no suggestion in Wang et al. that lovastatin directly enhances bone formation.

An abstract entitled "Lovastatin Prevents Steroid-Induced Adipogenesis and Osteoporosis" by Cui, Q. et al. appeared in the Reports of the ASBMR 18th Annual Meeting (September 1996) *J Bone Mineral Res.* (1996)11(S1):S510. The abstract reports that lovastatin diminished triglyceride vesicles that accumulated when osteoprogenitor cells cloned from bone marrow stroma of chickens were treated in culture with dexamethasone. Lovastatin was reported to diminish the expression of certain mRNAs and to allow the cells to maintain the osteogenic phenotype after dexamethasone treatment. Further, chickens that had undergone bone loss in the femoral head as a result of dexamethasone treatment were improved by treatment with lovastatin. Again, there is no suggestion that lovastatin directly enhances bone formation in the absence of steroid treatment.

In any event, these data are contrary to reports that dexamethasone and other inducers, such as BMPs, induce osteoblastic differentiation and stimulate osteocalcin mRNA (Bellows, C. G., et al., *Develop Biol* (1990) 140:132–38; Rickard, D. J., et al., *Develop Biol* (1994) 161:218–28). In addition, Ducy, P. et al., *Nature* (1996) 382:448–52 have recently reported that osteocalcin deficient mice exhibit a phenotype marked by increased bone formation and bones of improved functional quality, without impairment of bone resorption. Ducy et al. state that their data suggest that osteocalcin antagonists may be of therapeutic use in conjunction with estrogen replacement therapy (for prevention or treatment of osteoporosis).

The present invention discloses compounds useful for stimulating bone formation without the drawbacks associated with presently known treatments for bone deficit conditions. The ability of the invention compounds to stimulate bone growth affirmatively, as opposed to simply inhibiting resorption or stabilizing bone mass is an important advantage. This advantage can be realized when the compounds are supplied alone, or when they are supplied in combination with other agents which may enhance and complement their effects.

DISCLOSURE OF THE INVENTION

The invention provides compounds that can be administered as ordinary pharmaceuticals and have the metabolic effect of directly enhancing bone growth. The compounds of the invention can be identified using an assay for their ability to activate control elements associated with endogenous factors that stimulate bone growth. Thus, the invention is directed to methods and compositions for stimulating the growth of skeletal (bone) tissue, which methods and compositions use, as at least one of the active ingredients, a compound of the formula:

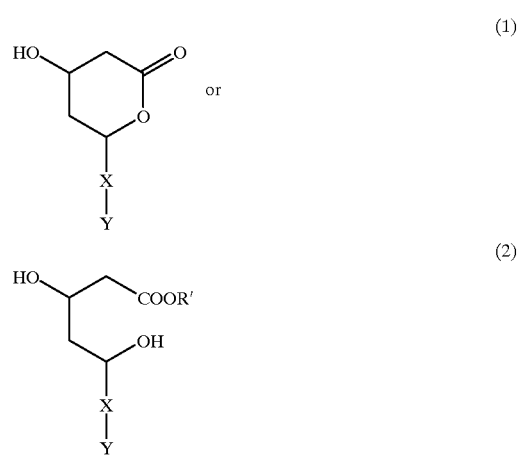

wherein X in each of formulas (1) and (2) represents a substituted or unsubstituted alkylene, alkenylene, or alkynylene linker of 2–6 C;

Y represents one or more carbocyclic or heterocyclic rings; when two or more rings are present in Y, they may optionally be fused; and R' represents a cation, H or a substituted or unsubstituted alkyl group of 1–6 C; and the dotted lines represent optional π-bonds.

Thus, the invention is directed to methods to treat bone disorders by directly stimulating bone formation using the compounds described and to pharmaceutical compositions for this use.

In another aspect, the invention is directed to methods to treat bone disorders by administering the above compounds of formulas (1) or (2) in combination with additional compounds and materials that complement their effects. These additional materials include small molecules that enhance bone formation or inhibit resorption such as those described in PCT application WO98/17267, published Apr. 30, 1998, and incorporated herein by reference; estrogen-related compounds which are known to inhibit bone resorption and bisphosphonates which are also known for this purpose.

MODES OF CARRYING OUT THE INVENTION

Figure 1:
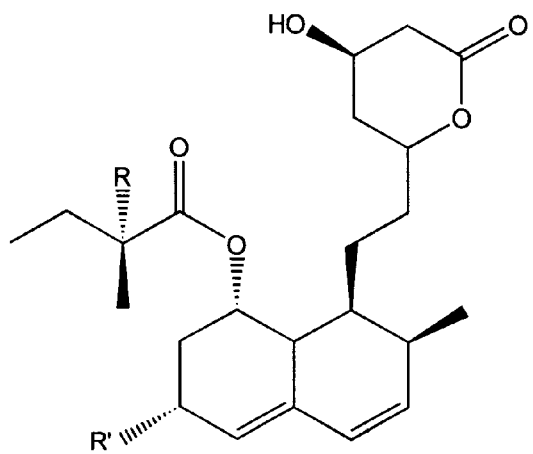
FIG. 1 shows the structure and activity (in the ABA screening assay of Example 1) of several compounds of the invention.
Figure 1:
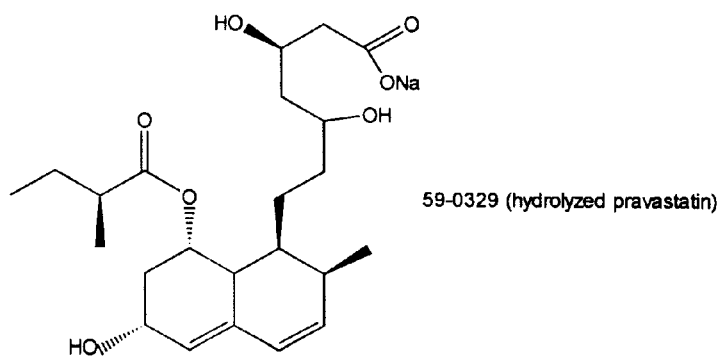
Figure 1:
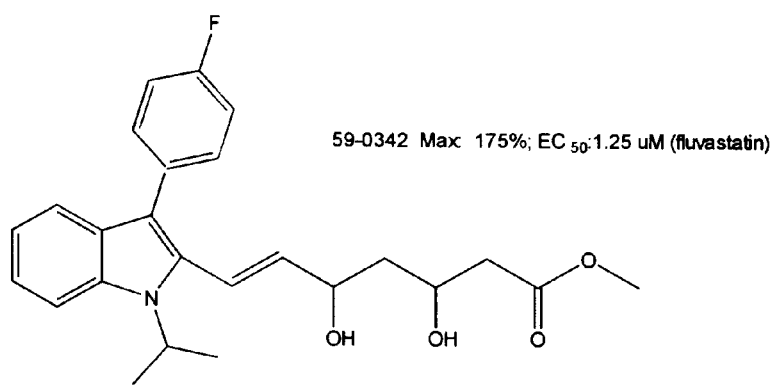

A rapid throughput screening test for compounds that stimulate bone formation by demonstration that they are capable of stimulating expression of a reporter gene linked to a BMP promoter (a surrogate for the production of bone morphogenetic factors that are endogenously produced) is described in U.S. application Ser. No. 08/458,434, filed Jun. 2, 1995, the entire contents of which are incorporated herein by reference. This assay is also described as a portion of a study of immortalized murine osteoblasts (derived from a mouse expressing a transgene composed of a BMP2 promoter driving expression of T-antigen) in Ghosh-Choudhery, N. et al. *Endocrinology* (1996) 137:331–39. In this study, the immortalized cells were stably transfected with a plasmid containing a luciferase reporter gene driven by a mouse BMP2 promoter (–2736/114 bp), and responded in a dose-dependent manner to recombinant human BMP2.

Briefly, the assay utilizes cells transformed permanently or transiently with constructs in which the promoter of a bone morphogenetic protein, specifically BMP2 or BMP4, is coupled to a reporter gene, typically luciferase. These transformed cells are then evaluated for the production of the reporter gene product; compounds that activate the BMP promoter will drive production of the reporter protein, which can be readily assayed. Many thousands of compounds have been subjected to this rapid screening technique, and only a very small percentage are able to elicit a level of expression of reporter gene 5-fold greater than that produced by vehicle alone. Compounds that activate the BMP promoter fall into groups, where members of each group share certain structural characteristics not present in inactive compounds. The active compounds ("BMP promoter-active compounds" or "active compounds") are useful in promoting bone or cartilage growth, and thus in the treatment of vertebrates in need of bone or cartilage growth. A number of these groups are disclosed in the above-referenced PCT applications WO98/17267 published Apr. 30, 1998; WO97/15308 published May 1, 1997; and WO97/48694 published Dec. 24, 1997.

BMP promoter-active compounds can be examined in a variety of other assays that test specificity and toxicity. For instance, non-BMP promoters or response elements can be linked to a reporter gene and inserted into an appropriate host cell. Cytotoxicity can be determined by visual or microscopic examination of BMP promoter- and/or non-BMP promoter-reporter gene-containing cells, for instance. Alternatively, nucleic acid and/or protein synthesis by the cells can be monitored. For in vivo assays, tissues may be removed and examined visually or microscopically, and optionally examined in conjunction with dyes or stains that facilitate histologic examination. In assessing in vivo assay results, it may also be useful to examine biodistribution of the test compound, using conventional medicinal chemistry/animal model techniques.

As used herein, "treat" or "treatment" include a postponement of development of bone deficit symptoms and/or a reduction in the severity of such symptoms that will or are expected to develop. The terms further include ameliorating existing bone or cartilage deficit symptoms, preventing additional symptoms, ameliorating or preventing the underlying metabolic causes of symptoms, preventing or reversing bone resorption and/or encouraging bone growth. Thus, the terms denote that a beneficial result has been conferred on a vertebrate subject with a cartilage, bone or skeletal deficit, or with the potential to develop such deficit.

By "bone deficit" is meant an imbalance in the ratio of bone formation to bone resorption, such that, if unmodified, the subject will exhibit less bone than desirable, or the subject's bones will be less intact and coherent than desired. Bone deficit may also result from fracture, from surgical intervention or from dental or periodontal disease. By "cartilage defect" is meant damaged cartilage, less cartilage than desired, or cartilage that is less intact and coherent than desired. "Bone disorders" includes both bone deficits and cartilage defects.

Representative uses of the compounds and combinations of the present invention include: repair of bone defects and deficiencies, such as those occurring in closed, open and non-union fractures; prophylactic use in closed and open fracture reduction; promotion of bone healing in plastic surgery; stimulation of bone ingrowth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; and treatment of other skeletal disorders, such as age-related osteoporosis, post-menopausal osteoporosis, glucocorticoid-induced osteoporosis or disuse osteoporosis and arthritis, or any condition that benefits from stimulation of bone formation. The compounds and combinations of the present invention can also be useful in repair of congenital, trauma-induced or surgical resection of bone (for instance, for cancer treatment), and in cosmetic surgery. Further, the compounds and combinations of the present invention can be used for limiting or treating cartilage defects or disorders, and may be useful in wound healing or tissue repair.

The compositions of the invention may be administered to vertebrates systemically or locally. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three times daily. Alternatively, the compounds disclosed herein may be administered in a cyclical manner (administration of disclosed compound; followed by no administration; followed by administration of disclosed compound, and the like). Treatment will continue until the desired outcome is achieved. In general, pharmaceutical formulations will include a compound of the present invention in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in *Remington's Pharmaceutical Sciences*, latest edition, Mack Publishing Co., Easton Pa., which is incorporated herein by reference. Pharmaceutical compositions for use within the present invention can be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid, or the like. For local administration, the delivery vehicle preferably provides a matrix for the growing bone or cartilage, and more preferably is a vehicle that can be absorbed by the subject without adverse effects.

Delivery of compounds herein to wound sites may be enhanced by the use of controlled-release compositions, such as those described in PCT publication WO 93/20859, incorporated herein by reference. Films of this type are particularly useful as coatings for prosthetic devices and surgical implants. The films may, for example, be wrapped around the outer surfaces of surgical screws, rods, pins, plates and the like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

In addition to the copolymers and carriers noted above, the biodegradable films and matrices may include other active or inert components. Of particular interest are those agents that promote tissue growth or infiltration, such as growth factors. Exemplary growth factors for this purpose include epidermal growth factor (EGF), fibroblast growth factor (FGF), platelet-derived growth factor (PDGF), transforming growth factors (TGFs), parathyroid hormone (PTH), leukemia inhibitory factor (LIF), insulin-like growth factors (IGFs) and the like. Agents that promote bone growth, such as bone morphogenetic proteins (U.S. Pat. No. 4,761,471; PCT Publication WO 90/11366), osteogenin (Sampath et al. *Proc. Natl. Acad. Sci. USA* (1987) 84:7109–13) and NaF (Tencer et al. *J. Biomed. Mat. Res.* (1989) 23:571–89) are also contemplated. Biodegradable films or matrices include calcium sulfate, tricalcium phosphate, hydroxyapatite, polylactic acid, polyanhydrides, bone or dermal collagen, pure proteins, extracellular matrix components and the like and combinations thereof. Such biodegradable materials may be used in combination with non-biodegradable materials, to provide desired mechanical, cosmetic or tissue or matrix interface properties.

Alternative methods for delivery of compounds of the present invention include use of ALZET osmotic minipumps (Alza Corp., Palo Alto, Calif.); sustained release matrix materials such as those disclosed in Wang et al. (PCT Publication WO 90/11366); electrically charged dextran beads, as disclosed in Bao et al. (PCT Publication WO 92/03125); collagen-based delivery systems, for example, as disclosed in Ksander et al. *Ann. Surg.* (1990) 211(3):288–94; methylcellulose gel systems, as disclosed in Beck et al. *J. Bone Min. Res.* (1991) 6(11):1257–65; alginate-based systems, as disclosed in Edelman et al. *Biomaterials* (1991) 12:619–26 and the like. Other methods well known in the art for sustained local delivery in bone include porous coated metal prostheses that can be impregnated and solid plastic rods with therapeutic compositions incorporated within them.

The compounds of the present invention may also be used in conjunction with agents that inhibit bone resorption. Antiresorptive agents, such as estrogen, bisphosphonates and calcitonin, are preferred for this purpose. More specifically, the compounds disclosed herein may be administered for a period of time (for instance, months to years) sufficient to obtain correction of a bone deficit condition. Once the bone deficit condition has been corrected, the vertebrate can be administered an anti-resorptive compound to maintain the corrected bone condition. Alternatively, the compounds disclosed herein may be administered with an anti-resorptive compound in a cyclical manner (administration of disclosed compound, followed by anti-resorptive, followed by disclosed compound, and the like).

In additional formulations, conventional preparations such as those described below may be used.

Aqueous suspensions may contain the active ingredient in admixture with pharmacologically acceptable excipients, comprising suspending agents, such as methyl cellulose; and wetting agents, such as lecithin, lysolecithin or long-chain fatty alcohols. The said aqueous suspensions may also contain preservatives, coloring agents, flavoring agents, sweetening agents and the like in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise sterile or sterilized products. Injectable compositions may be provided containing the active compound and any of the well known injectable carriers. These may contain salts for regulating the osmotic pressure.

If desired, the osteogenic agents can be incorporated into liposomes by any of the reported methods of preparing liposomes for use in treating various pathogenic conditions. The present compositions may utilize the compounds noted above incorporated in liposomes in order to direct these compounds to macrophages, monocytes, as well as other cells and tissues and organs which take up the liposomal composition. The liposome-incorporated compounds of the invention can be utilized by parenteral administration, to allow for the efficacious use of lower doses of the compounds. Ligands may also be incorporated to further focus the specificity of the liposomes.

Suitable conventional methods of liposome preparation include, but are not limited to, those disclosed by Bangham, A. D. et al. *J Mol Biol* (1965) 23:238–252, Olson, F. et al. *Biochim Biophys Acta* (1979) 557:9–23, Szoka, F. et al. *Proc Natl Acad Sci USA* (1978) 75:4194–4198, Kim, S. et al. *Biochim Biophys Acta* (1983) 728:339:348, and Mayer, et al. *Biochim Biophys Acta* (1986) 858:161–168.

The liposomes may be made from the present compounds in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol and the like. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio) propane (DOTAP), N-[1-(2,3-dioleoyl) propyl-N,N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of the present compounds incorporated into the lipid layer of liposomes can be varied with the concentration of the lipids ranging from about 0.01 to about 50 mole percent.

The liposomes with the above formulations may be made still more specific for their intended targets with the incorporation of monoclonal antibodies or other ligands specific for a target. For example, monoclonal antibodies to the BMP receptor may be incorporated into the liposome by linkage to phosphatidylethanolamine (PE) incorporated into the liposome by the method of Leserman, L. et al. *Nature* (1980) 288:602–604.

Veterinary uses of the disclosed compounds are also contemplated. Such uses would include treatment of bone or cartilage deficits or defects, i.e., bone disorders, in domestic animals, livestock and thoroughbred horses.

The compounds of the present invention may be used to stimulate growth of bone-forming cells or their precursors, or to induce differentiation of bone-forming cell precursors, either in vitro or ex vivo. The compounds described herein may also modify a target tissue or organ environment, so as to attract bone-forming cells to an environment in need of such cells. As used herein, the term "precursor cell" refers to a cell that is committed to a differentiation pathway, but that generally does not express markers or function as a mature, fully differentiated cell. As used herein, the term "mesenchymal cells" or "mesenchymal stem cells" refers to pluripotent progenitor cells that are capable of dividing many times, and whose progeny will give rise to skeletal tissues, including cartilage, bone, tendon, ligament, marrow stroma and connective tissue (see A. Caplan *J. Orthop. Res.* (1991) 9:641–50). As used herein, the term "osteogenic cells" includes osteoblasts and osteoblast precursor cells. More particularly, the disclosed compounds are useful for stimulating a cell population containing marrow mesenchymal cells, thereby increasing the number of osteogenic cells in that cell population. In a preferred method, hematopoietic cells are removed from the cell population, either before or after stimulation with the disclosed compounds. Through practice of such methods, osteogenic cells may be expanded. The expanded osteogenic cells can be infused (or reinfused) into a vertebrate subject in need thereof. For instance, a subject's own mesenchymal stem cells can be exposed to compounds of the present invention ex vivo, and the resultant osteogenic cells could be infused or directed to a desired site within the subject, where further proliferation and/or differentiation of the osteogenic cells can occur without immunorejection. Alternatively, the cell population exposed to the disclosed compounds may be immortalized human fetal osteoblastic or osteogenic cells. If such cells are infused or implanted in a vertebrate subject, it may be advantageous to "immunoprotect" these non-self cells, or to immunosuppress (preferably locally) the recipient to enhance transplantation and bone or cartilage repair.

Within the present invention, an "effective amount" of a composition is that amount which produces a statistically significant effect. For example, an "effective amount" for therapeutic uses is the amount of the composition comprising an active compound herein required to provide a clinically significant increase in healing rates in fracture repair; reversal of bone loss in osteoporosis; reversal of cartilage defects or disorders; prevention or delay of onset of osteoporosis; stimulation and/or augmentation of bone formation in fracture non-unions and distraction osteogenesis; increase and/or acceleration of bone growth into prosthetic devices; and repair of dental defects. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds of the invention (for example, in osteoporosis where an increase in bone formation is desired) is manifested as a statistically significant difference in bone mass between treatment and control groups. This difference in bone mass may be seen, for example, as a 5–20% or more increase in bone mass in the treatment group. Other measurements of clinically significant increases in healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models of the disease of interest.

The dosage of the compounds of the invention will vary according to the extent and severity of the need for treatment, the activity of the administered compound, the general health of the subject, and other considerations well known to the skilled artisan. Generally, they can be administered to a typical human on a daily basis as an oral dose of about 0.1 mg/kg-1000 mg/kg, and more preferably from about 1 mg/kg to about 200 mg/kg. The parenteral dose will appropriately be 20–100% of the oral dose. While oral administration may be preferable in most instances (for reasons of ease, patient acceptability, and the like), alternative methods of administration may be appropriate for selected compounds and selected defects or diseases. In comparative assays, positive control compounds or other bone-active test compounds may be administered subcutaneously, while statin-type test compounds are administered orally.

Screening Assays

The osteogenic activity of the compounds used in the methods of the invention can be verified using in vitro screening techniques, such as the assessment of transcription of a reporter gene coupled to a bone morphogenetic protein-associated promoter, as described above, or in alternative assays such as the following:

Neonatal Mouse Calvaria Assay (In vitro)

An assay for bone resorption or bone formation is similar to that described by Gowen M. & Mundy G. *J Immunol* (1986) 136:2478–82. Briefly, four days after birth, the front and parietal bones of ICR Swiss white mouse pups are removed by microdissection and split along the sagittal suture. In an assay for resorption, the bones are incubated in BGJb medium (Irvine Scientific, Santa Ana, Calif.) plus 0.02% (or lower concentration) β-methylcyclodextrin, wherein the medium also contains test or control substances. The medium used when the assay is conducted to assess bone formation is Fitton and Jackson Modified BGJ Medium (Sigma) supplemented with 6 μg/ml insulin, 6 μg/ml transferrin, 6 ng/ml selenous acid, calcium and phosphate concentrations of 1.25 and 3.0 mM, respectively, and ascorbic acid to a concentration of 100 μg/ml is added every two days. The incubation is conducted at 37° C. in a humidified atmosphere of 5% $CO_2$ and 95% air for 96 hours.

Following this, the bones are removed from the incubation media and fixed in 10% buffered formalin for 24–48 hours, decalcified in 14% EDTA for 1 week, processed through graded alcohols; and embedded in paraffin wax. Three μm sections of the calvaria are prepared. Representative sections are selected for histomorphometric assessment of bone formation or bone resorption. Bone changes are measured on sections cut 200 μm apart. Osteoblasts and osteoclasts are identified by their distinctive morphology.

Other auxiliary assays can be used as controls to determine non-BMP promoter-mediated effects of test compounds. For example, mitogenic activity can be measured using screening assays featuring a serum-response element (SRE) as a promoter and a luciferase reporter gene. More specifically, these screening assays can detect signaling through SRE-mediated pathways, such as the protein kinase C pathway. For instance, an osteoblast activator SRE-luciferase screen and an insulin mimetic SRE-luciferase screen are useful for this purpose. Similarly, test compound stimulation of cAMP response element (CRE)-mediated pathways can also be assayed. For instance, cells transfected with receptors for PTH and calcitonin (two bone-active agents) can be used in CRE-luciferase screens to detect elevated cAMP levels. Thus, the BMP promoter specificity of a test compound can be examined through use of these types of auxiliary assays.

In vivo Assay of Effects of Compounds on Murine Calvarial Bone Growth

Male ICR Swiss white mice, aged 4–6 weeks and weighing 13–26 gm, are employed, using 4–5 mice per group. The calvarial bone growth assay is performed as described in PCT application WO 95/24211, incorporated by reference. Briefly, the test compound or appropriate control vehicle is injected into the subcutaneous tissue over the right calvaria of normal mice. Typically, the control vehicle is the vehicle in which the compound was solubilized, and is PBS containing 5% DMSO or is PBS containing Tween (2 μl/10 ml). The animals are sacrificed on day 14 and bone growth measured by histomorphometry. Bone samples for quantitation are cleaned from adjacent tissues and fixed in 10% buffered formalin for 24–48 hours, decalcified in 14% EDTA for 1–3 weeks, processed through graded alcohols; and embedded in paraffin wax. Three to five μm sections of the calvaria are prepared, and representative sections are selected for histomorphometric assessment of the effects on bone formation and bone resorption. Sections are measured by using a camera lucida attachment to trace directly the microscopic image onto a digitizing plate. Bone changes are measured on sections cut 200 μm apart, over 4 adjacent 1×1 mm fields on both the injected and noninjected sides of the calvaria. New bone is identified by its characteristic woven structure, and osteoclasts and osteoblasts are identified by their distinctive morphology. Histomorphometry software (OsteoMeasure, Osteometrix, Inc., Atlanta) is used to process digitizer input to determine cell counts and measure areas or perimeters.

Additional In Vivo Assays

Lead compounds can be further tested in intact animals using an in vivo, dosing assay. Prototypical dosing may be accomplished by subcutaneous, intraperitoneal or oral administration, and may be performed by injection, sustained release or other delivery techniques. The time period for administration of test compound may vary (for instance, 28 days as well as 35 days may be appropriate). An exemplary, in vivo oral or subcutaneous dosing assay may be conducted as follows:

In a typical study, 70 three-month-old female Sprague-Dawley rats are weight-matched and divided into seven groups, with ten animals in each group. This includes a baseline control group of animals sacrificed at the initiation of the study; a control group administered vehicle only; a PBS-treated control group; and a positive control group administered a compound (non-protein or protein) known to promote bone growth. Three dosage levels of the compound to be tested are administered to the remaining three groups.

Briefly, test compound, positive control compound, PBS, or vehicle alone is administered subcutaneously once per day for 35 days. All animals are injected with calcein nine days and two days before sacrifice (two injections of calcein administered each designated day). Weekly body weights are determined. At the end of the 35-day cycle, the animals are weighed and bled by orbital or cardiac puncture. Serum calcium, phosphate, osteocalcin, and CBCs are determined. Both leg bones (femur and tibia) and lumbar vertebrae are removed, cleaned of adhering soft tissue, and stored in 70% ethanol for evaluation, as performed by peripheral quantitative computed tomography (pQCT; Ferretti, J. Bone (1995) 17:353S-64S), dual energy X-ray absorptiometry (DEXA; Laval-Jeantet A. et al. Calcif Tissue Intl (1995) 56:14–18; J. Casez et al. Bone and Mineral (1994) 26:61–68) and/or histomorphometry. The effect of test compounds on bone remodeling can thus be evaluated.

Lead compounds can also be tested in acute ovariectomized animals (prevention model) using an in vivo dosing assay. Such assays may also include an estrogen-treated group as a control. An exemplary subcutaneous dosing assay is performed as follows:

In a typical study, 80 three-month-old female Sprague-Dawley rats are weight-matched and divided into eight groups, with ten animals in each group. This includes a baseline control group of animals sacrificed at the initiation of the study; three control groups (sham ovariectomized (sham OVX)+vehicle only; ovariectomized (OVX)+vehicle only; PBS-treated OVX); and a control OVX group that is administered a compound known to promote bone growth. Three dosage levels of the compound to be tested are administered to the remaining three groups of OVX animals.

Since ovariectomy (OVX) induces hyperphagia, all OVX animals are pair-fed with sham OVX animals throughout the 35 day study. Briefly, test compound, positive control compound, PBS, or vehicle alone is administered orally or subcutaneously once per day for 35 days. Alternatively, test compound can be formulated in implantable pellets that are implanted for 35 days, or may be administered orally, such as by gastric gavage. All animals, including sham OVX/vehicle and OVX/vehicle groups, are injected intraperitoneally with calcein nine days and two days before sacrifice (two injections of calcein administered each designated day, to ensure proper labeling of newly formed bone). Weekly body weights are determined. At the end of the 35-day cycle, the animals' blood and tissues are processed as described above.

Lead compounds may also be tested in chronic OVX animals (treatment model). An exemplary protocol for treatment of established bone loss in ovariectomized animals that can be used to assess efficacy of anabolic agents may be performed as follows. Briefly, 80 to 100 six month old female, Sprague-Dawley rats are subjected to sham surgery (sham OVX) or ovariectomy (OVX) at time 0, and 10 rats are sacrificed to serve as baseline controls. Body weights are recorded weekly during the experiment. After approximately 6 weeks (42 days) or more of bone depletion, 10 sham OVX and 10 OVX rats are randomly selected for sacrifice as depletion period controls. Of the remaining animals, 10 sham OVX and 10 OVX rats are used as placebo-treated controls. The remaining OVX animals are treated with 3 to 5 doses of test drug for a period of 5 weeks (35 days). As a positive control, a group of OVX rats can be treated with an agent such as PTH, a known anabolic agent in this model (Kimmel et al. Endocrinology (1993) 132:1577–84). To determine effects on bone formation, the following procedure can be followed. The femurs, tibiae and lumbar vertebrae 1 to 4 are excised and collected. The proximal left and right tibiae are used for pQCT measurements, cancellous bone mineral density (BMD) (gravimetric determination), and histology, while the midshaft of each tibiae is subjected to cortical BMD or histology. The femurs are prepared for pQCT scanning of the midshaft prior to biomechanical testing. With respect to lumbar vertebrae (LV), LV2 are processed for BMD (pQCT may also be performed); LV3 are prepared for undecalcified bone histology; and LV4 are processed for mechanical testing.

Nature of the Compounds Useful in the Invention

The compounds useful in the methods and compositions of the invention are of the formula:

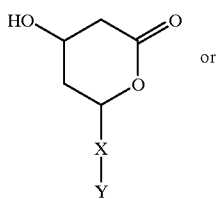
(1)

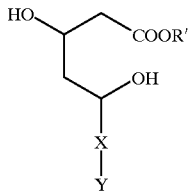
(2)

wherein X in each of formulas (1) and (2) represents a substituted or unsubstituted alkylene, alkenylene, or alkynylene linker of 2–6 C;

Y represents one or more carbocyclic or heterocyclic rings; when Y comprises two or more rings, they may optionally be fused; and R' represents a cation, H or a substituted or unsubstituted alkyl group of 1–6 C; and the dotted lines represent optional π-bonds. It is understood that if R' represents a cation with multiple positive charges, the appropriate number of anions is coupled with it. Preferred substituents on X or on R' when R' is alkyl are hydroxy, alkoxy, phenyl, amino and alkyl- or dialkylamino.

The compounds useful in the invention contain at least one and generally several chiral centers. Compounds useful in the invention include mixtures of the various stereoisomers and the stereoisomeric forms of the compounds individually. Preferred stereoisomers with respect to the compound of formula (1) in forms which do not contain π-bonds are of the formula:

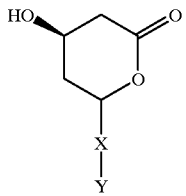
(3)

and the corresponding stereochemistry in the open chain (nonlactone) form of formula (2).

Forms of formulas (1) and (2) which do not contain π-bonds (other than in X or Y) are themselves preferred.

In one set of preferred embodiments, X is unsubstituted; most preferably X is selected from the group consisting of —CH$_2$CH$_2$—; —CH=CH—; and —C≡C—, especially —CH$_2$CH$_2$—.

Preferred embodiments of Y comprise ring systems such as naphthyl, polyhydronaphthyl, monohydro- or dihydrophenyl, quinolyl, pyridyl, quinazolyl, pteridyl, pyrolyl, oxazoyl and the like and the reduced or partially reduced forms thereof.

Preferred embodiments of the substituent Y include those of the formula:

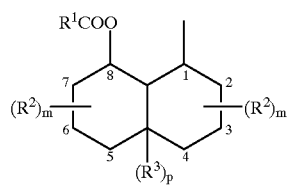
(4)

wherein $R^1$ is substituted or unsubstituted alkyl;

each $R^2$ is independently a noninterfering substituent;

$R^3$ is H, hydroxy, or alkoxy (1–6 C);

each m is independently an integer of 0–6, wherein each $R^2$ may reside in any of positions 2–7; and p is 0 or 1, depending on the position of any π-bonds indicated by the dotted lines.

Particularly preferred embodiments include those of formulas (4a)–(4f) wherein the upper limit of n is adjusted according to the valence requirements appropriate for the particular ring system.

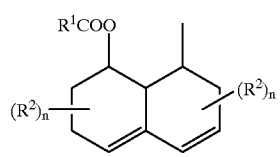
(4a)

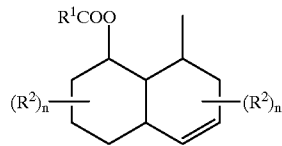
(4b)

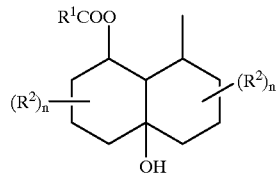
(4c)

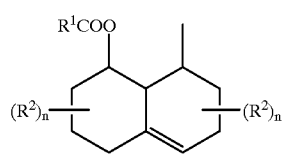
(4d)

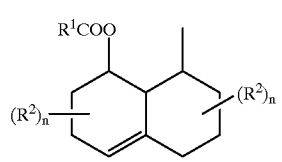
(4e)

(4f)

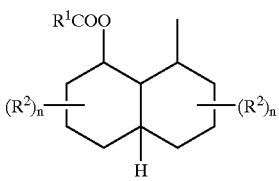

While $R^1$ may be substituted alkyl, wherein the substituents may include hydroxy, alkoxy, alkylthiol, phenyl, phenylalkyl, and halo, unsubstituted alkyl is preferred. Particularly preferred embodiments of $R^1$ are alkyl of 1–6 C, including propyl, sec-butyl, t-butyl, n-butyl, isobutyl, pentyl, isopentyl, 1-methylbutyl, and 2-methylbutyl. Particularly preferred are propyl and sec-butyl.

Preferred embodiments for $R^2$ include hydroxy, =O, and substituted or unsubstituted lower alkyl (1–4 C), in particular methyl, and hydroxymethyl. In the preferred embodiments, each n is independently 1 or 2 and preferred positions for substitution are positions 2 and 6 (see formula (4)).

As indicated above, the compounds of the invention may be supplied as individual stereoisomers or as mixtures of stereoisomers. Preferred stereoisomers are those of the formulas (4g) and (4h) as typical and appropriate for those represented by the formulas (4a)–(4f).

(4g)

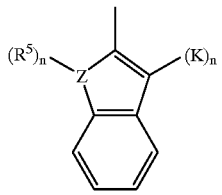

(4h)

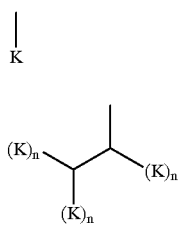

Particularly preferred are compounds with the stereochemistry of formulas (4g) and (4h) wherein the noted substituents are the sole substituents on the polyhydronaphthyl system optionally including additional substituents at position 5. Preferred embodiments include those wherein each $R^2$ is independently OH, $CH_2OH$, methyl, or =O. Preferred embodiments of $R^1$ in these preferred forms are propyl and sec-butyl.

Additional preferred embodiments of Y include:

(5)

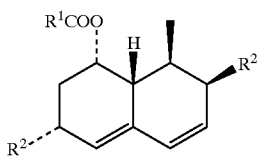

(6)

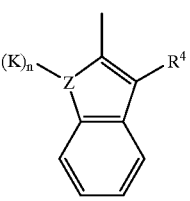

(7)

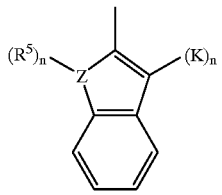

(8)

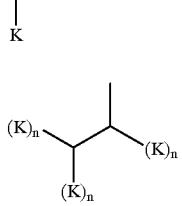

(9)

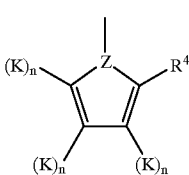

wherein Z is CH or N (when n associated with its extra-ring substituent is 1) or is S or O (when said n is 0). Each K comprises a substituted or unsubstituted aromatic or nonaromatic carbocyclic or heterocyclic ring system which may optionally be spaced from the linkage position shown in formulas (5)–(9) by a linker of 1–2 C, including —CHOH—; —CO—; and —CHNH$_2$—, for example. Aromatic ring systems are preferred. Particularly preferred are compounds of formula (7), especially when both n are 1.

Each of $R^4$ and $R^5$ is independently H or linear or branched chain substituted or unsubstituted alkyl, wherein substituents are preferably hydroxy, alkoxy, phenyl, amino and alkyl- or dialkylamino. Each n is independently 0 or 1; however, at least one n in formula (5) and in formula (9) must be 1.

The substituents on the aromatic ring systems or nonaromatic ring systems of the invention can be any noninterfering substituents. Generally, the non-interfering substituents can be of wide variety. Among substituents that do not interfere with the beneficial effect of the compounds of the invention on bone formation in treated subjects include alkyl (1–6 C, preferably lower alkyl 1–4 C), including straight or branched-chain forms thereof, alkenyl (2–6 C, preferably 2–4 C), alkynyl (2–6 C, preferably 2–4 C), all of which can be straight or branched chains and may contain further substituents; halogens, including F, Cl, Br and I; silyloxy, OR, SR, $NR_2$, OOCR, COOR, NCOR, NCOOR, and benzoyl, $CF_3$, $OCF_3$, $SCF_3$, $N(CF_3)_2$, CN, SO, $SO_2R$ and $SO_3R$ wherein R is alkyl (1–6 C) or is H. Where two substituents are in adjacent positions in the aromatic or nonaromatic system, they may form a ring. Further, rings not fused to the aromatic or nonaromatic system may be included in substituents which contain sufficient carbon atoms and heteroatoms to provide this possibility.

Preferred non-interfering substituents include hydrocarbyl groups of 1–6 C, including saturated and unsaturated, linear or branched hydrocarbyl as well as hydrocarbyl groups containing ring systems; halo groups, alkoxy, hydroxy, CN, CF$_3$, and COOR, amino, monoalkyl- and dialkylamino where the alkyl groups are 1–6 C.

Although the number of substituents on a ring symbolized by K may typically be 0–4 or 0–5 depending on the available positions, preferred embodiments include those wherein the number on a single ring is 0, 1 or 2, preferably 0 or 1.

The compounds useful in the methods and compositions of the invention can be synthesized by art-known methods as they resemble a class of compounds known in the art to behave as antihypercholesterolemic agents. Typical among these is lovastatin, marketed by Merck as Mevacor®. The synthesis of lovastatin and various analogs thereof is set forth in U.S. Pat. No. 4,963,538, incorporated herein by reference. In addition, methods for synthesis of lovastatin and analogous compounds such as compactin (mevastatin), simvastatin, and pravastatin are set forth in U.S. Pat. Nos. 5,059,696; 4,873,345; 4,866,186; 4,894,466; 4,894,465; 4,855,456; and 5,393,893, all incorporated herein by reference. Certain of these compounds are also produced by microorganisms as described in U.S. Pat. Nos. 5,362,638; 5,409,820; 4,965,200; and 5,409,820, all also incorporated herein by reference. Compounds described as end-products in these documents are useful in the methods of the invention.

Additional analogs, including those containing aromatic embodiments of Y, are described in U.S. Pat. No. 5,316,765 incorporated herein by reference. For example, the preparation of fluvastatin is described in PCT Application WO84/02131. Other compounds are described in, for example, Roth, B. D. et al., *J Med Chem* (1991) 34:357–366; Krause, R. et al, *J Drug Dev* (1990) 3(Suppl. 1):255–257; Karanewsky, D. S. et al., *J Med Chem* (1990) 33:2952–2956.

Particularly preferred are lovastatin (59-0326), mevastatin (59-0327), simvastatin (59-0328) and fluvastatin (59-0342), shown in FIG. 1.

Combinations

As set forth above, the compounds of the present invention of formulas (1) and (2) are advantageously administered in combination with additional active ingredients which complement or enhance their effect. One group of compounds of this type is of the general formula

wherein each of Ar$^1$ and Ar$^2$ is independently a substituted or unsubstituted phenyl, substituted or unsubstituted naphthyl, a substituted or unsubstituted aromatic system containing a six-membered heterocycle or a substituted or unsubstituted aromatic system containing a five-membered heterocycle and wherein L is a linker which spaces Ar$^1$ from Ar$^2$ at a distance of 1.5–15 Å. Preferred embodiments of these compounds include those wherein Ar$^1$ is a bicyclic system in which one of the rings is benzene fused to a heterocycle containing nitrogen, oxygen, and/or sulfur. Particularly preferred are benzimidazoles, indoles, quinolines, isoquinolines, pteridines and the like. Compounds in which both Ar$^1$ and Ar$^2$ are phenyl are also preferred. Particularly preferred are compounds of the formulas 59-0098, 59-0145 and 59-0203.

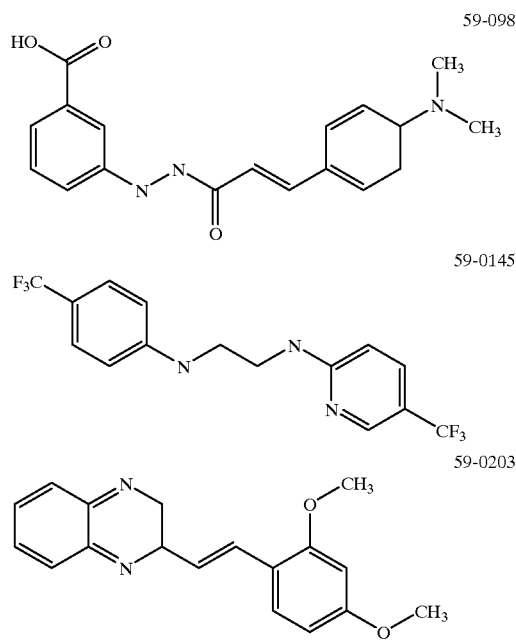

The proportion of the compounds of formulas (1) and (2) to the compound of formula (10) is dependent on the nature of the condition and the particular choice for each of these compounds. However, ratios for compounds of formulas (1) or (2) (or mixtures thereof) to compounds of formula (10) (or mixtures thereof) are in the range of 100:1–1:100, preferably 10:1–1:10. This combination is particularly effective since the mechanisms of action of these compounds may be different.

In another embodiment, the compounds of formulas (1) and (2) can be combined with estrogens or estrogen-related compounds since estrogens are known to inhibit bone resorption. Typical estrogen compounds include estradiol, progesterone, and analogs thereof as are well known in the art. The ratio of compounds of formulas (1) or (2) (or mixtures) to estrogens (or mixtures) are typically in the ranges set forth above.

Still another suitable combination is that of the compounds of formulas (1) and (2) with the bisphosphonates and related compounds such as those set forth in U.S. Pat. No. 5,312,814. Bisphosphonate compounds are generally known in the art and contain the linkage P-C-P such as represented by the formula

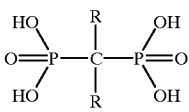

and the salts, esters and amides thereof, and thus differ from the pyrophosphates (P-O-P). Amidated forms are particularly preferred. Particularly preferred are ibandronate, risedronate, alandronate, pamidronate, and clodronate. These compositions also are formulated according to the condition to be treated and the selection of the active ingredient and are composed of similar ratios to those set forth above.

The administration of these additional compounds may be simultaneous with the administration of the compounds of formulas (1) and (2) of the invention or may be administered in tandem with the administration of the compounds of the invention. Any suitable protocol may be devised whereby the various compounds to be included in the combination treatment are administered within minutes, hours, days, or weeks of each other. Repeated administration in a cyclic protocol is also envisioned.

The following examples are intended to illustrate but not to limit the invention.

EXAMPLE 1

High Throughput Screening

Thousands of compounds have been tested in the assay system set forth in U.S. Ser. No. 08/458,434, filed Jun. 2, 1995, and incorporated herein by reference. Representative compounds of the invention gave positive responses, while the majority of (unrelated) compounds are inactive. In this screen, the standard positive control was the compound 59-0008 (also denoted "OS8"), which is of the formula:

"OS8"

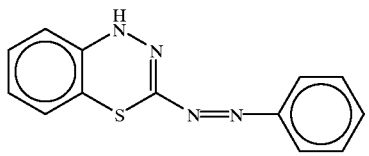

In more detail, the 2T3-BMP-2-LUC cells, a stably transformed osteoblast cell line described in Ghosh-Choudhury et al. *Endocrinology* (1996) 137:331–39, referenced above, was employed. The cells were cultured using α-MEM, 10% FCS with 1% penicillin/streptomycin and 1% glutamine ("plating medium"), and were split 1:5 once per week. For the assay, the cells were resuspended in a plating medium containing 4% FCS, plated in microtiter plates at a concentration of $5 \times 10^3$ cells (in 50 µl)/well, and incubated for 24 hours at 37° C. in 5% $CO_2$. To initiate the assay, 50 µl of the test compound or the control in DMSO was added at 2X concentration to each well, so that the final volume was 100 µl. The final serum concentration was 2% FCS, and the final DMSO concentration was 1%. Compound 59-0008 (10 µM) was used as a positive control.

The treated cells were incubated for 24 hours at 37° C. and 5% $CO_2$. The medium was then removed, and the cells were rinsed three times with PBS. After removal of excess PBS, 25 µl of 1X cell culture lysing reagent (Promega #E153A) was added to each well and incubated for at least ten minutes. Optionally, the plates/samples could be frozen at this point. To each well was added 50 µl of luciferase substrate (Promega #E152A; 10 ml Promega luciferase assay buffer per 7 mg Promega luciferase assay substrate). Luminescence was measured on an automated 96-well luminometer, and was expressed as either picograms of luciferase activity per well or as picograms of luciferase activity per microgram of protein.

In this assay, compound 59-0008 (3-phenylazo-1H-4,1,2-benzothiadiazine) exhibits a pattern of reactivity which is maximal at a concentration of approximately 3–10 µM. Accordingly, other tested compounds can be evaluated at various concentrations, and the results compared to the results obtained for 59-0008 at 10 µM (which value would be normalized to 100). Alternatively, the reactivity of a compound to be tested can be compared directly to a negative control containing no compound.

A variety of statin compounds (simvastatin designated OS114 or 59-0328, hydrolyzed simvastatin, mevastatin designated 59-0327, lovastatin designated 59-0326, fluvastatin designated 59-0342, and pravastatin designated 59-0329) were tested in the in vitro BMP-promoter based (designated "ABA") assay (as described at the beginning of this example above), and in some experiments were tested also in a control osteoblast/serum response element (OBSRE) cell-based assay and/or a control glucagon assay. In the negative control OBSRE assay, a murine osteoblast cell line, such as CCC-4 expressing a serum response element (SRE)-luciferase reporter gene is used (see WO96/07733). In the negative control glucagon assay, a glucagon receptor-positive BHK cell expressing a CRE-luciferase reporter gene is used (see U.S. Pat. No. 5,698,672).

The results of three separate determinations in the ABA assay are shown below. Most of the statins (i.e., simvastatin, hydrolyzed simvastatin, mevastatin, lovastatin, and fluvastatin) exhibited a dose-dependent stimulatory effect in the ABA assay, but not in control assays. In one experiment, simvastatin demonstrated over a 20-fold induction in the ABA assay, as compared to the non-statin, ABA stimulatory compound 59-0008.

| ABA Assay Results | | | | |
|---|---|---|---|---|
| | | Sample Concentration | % 59-0008 | Fold increase over negative |
| Experiment 1 | | µM | µg/ml | Response | control |
| Lovastatin 59-0326 | | 497 | 200 | −22.650 | −0.003 |
| | | 248.5 | 100 | −22.620 | −0.001 |
| | | 124.25 | 50 | −22.510 | 0.003 |
| | | 62.125 | 25 | 144.730 | 7.408 |
| | | 31.0625 | 12.5 | 153.790 | 7.809 |
| | | 15.5312 | 6.25 | 126.230 | 6.589 |
| | | 7.76562 | 3.125 | 111.730 | 5.947 |
| | | 3.88281 | 1.5625 | 67.080 | 3.970 |
| | | 1.94140 | 0.78125 | 35.220 | 2.559 |
| | | 0.97070 | 0.390625 | 27.830 | 2.232 |
| | | 0.48535 | 0.195312 | 22.840 | 2.011 |
| Mevastatin 59-0327 | | 512 | 200 | −1.600 | 0.929 |
| | | 256 | 100 | 12.460 | 1.552 |
| | | 128 | 50 | 153.110 | 7.779 |
| | | 64 | 25 | 152.690 | 7.760 |
| | | 32 | 12.5 | 164.730 | 8.293 |
| | | 16 | 6.25 | 140.260 | 7.210 |
| | | 8 | 3.125 | 99.670 | 5.413 |
| | | 4 | 1.5625 | 47.630 | 3.103 |
| | | 2 | 0.78125 | 34.520 | 2.528 |
| | | 1 | 0.390625 | 15.650 | 1.693 |
| | | 0.5 | 0.195312 | 25.840 | 2.144 |
| Simvastatin 59-0328 | | 477 | 200 | −22.960 | −0.009 |
| | | 238.5 | 100 | −23.010 | −0.011 |
| | | 119.25 | 50 | −22.950 | −0.008 |
| | | 59.625 | 25 | 148.310 | 7.515 |
| | | 29.8125 | 12.5 | 131.300 | 6.768 |
| | | 14.9062 | 6.25 | 141.970 | 7.237 |
| | | 7.45312 | 3.125 | 135.610 | 6.957 |
| | | 3.72656 | 1.5625 | 99.170 | 5.356 |
| | | 1.86328 | 0.78125 | 69.600 | 4.057 |
| | | 0.93164 | 0.390625 | 38.210 | 2.679 |
| | | 0.46582 | 0.195312 | 29.030 | 2.275 |
| Pravastatin 59-0329 | | 471 | 200 | 11.670 | 1.513 |
| | | 235.5 | 100 | 7.620 | 1.335 |
| | | 117.75 | 50 | 5.000 | 1.220 |
| | | 58.875 | 25 | 3.520 | 1.155 |
| | | 29.4375 | 12.5 | 1.110 | 1.049 |
| | | 14.7187 | 6.25 | 0.920 | 1.040 |
| | | 7.35937 | 3.125 | 0.380 | 1.017 |
| | | 3.67968 | 1.5625 | −1.120 | 0.951 |
| | | 0.83984 | 0.78125 | −1.980 | 0.913 |
| | | 0.91992 | 0.390625 | −1.290 | 0.943 |
| | | 0.45996 | 0.195312 | −4.390 | 0.807 |

-continued

| ABA Assay Results | | | |
|---|---|---|---|
| Fluvastatin | 470 | 200 | −22.700 | −0.005 |
| 59-0342 | 235 | 100 | −22.570 | 0.001 |
|  | 117.5 | 50 | −22.660 | −0.003 |
|  | 58.75 | 25 | 137.500 | 7.088 |
|  | 29.375 | 12.5 | 164.450 | 8.281 |
|  | 14.6875 | 6.25 | 165.630 | 8.333 |
|  | 7.34375 | 3.125 | 173.280 | 8.672 |
|  | 3.67187 | 1.5625 | 117.980 | 6.223 |
|  | 1.83593 | 0.78125 | 75.160 | 4.328 |
|  | 0.91796 | 0.390625 | 28.080 | 2.243 |
|  | 0.45898 | 0.195312 | 36.820 | 2.630 |
| Hydrolyzed | 477 | 200 | −15.140 | −0.0 |
| simvastatin | 238.5 | 100 | −15.230 | −0.0 |
|  | 119.25 | 50 | 44.520 | 3.9 |
|  | 59.625 | 25 | 200.230 | 14.3 |
|  | 29.8125 | 12.5 | 156.230 | 11.3 |
|  | 14.90625 | 6.25 | 150.260 | 10.9 |
|  | 7.453125 | 3.125 | 75.860 | 6.0 |
|  | 3.726562 | 1.5625 | 36.190 | 3.4 |
|  | 1.863281 | 0.78125 | 10.430 | 1.6 |
|  | 0.931640 | 0.390625 | 1.520 | 1.1 |
|  | 0.465820 | 0.195312 | −0.680 | 0.9 |

|  | Sample Concentration | | % 59-0008 | Fold increase over negative |
|---|---|---|---|---|
| Experiment 2 | $\mu$M | $\mu$g/ml | Response | control |
| Mevastatin | 100 | 39 | 88.860 | 6.9 |
| 59-0327 | 50 | 19.5 | 97.420 | 7.4 |
|  | 25 | 9.75 | 71.630 | 5.7 |
|  | 12.5 | 4.875 | 66.010 | 5.3 |
|  | 6.25 | 2.4375 | 36.210 | 3.4 |
|  | 3.125 | 1.21875 | 10.970 | 1.7 |
|  | 1.5625 | 0.609375 | 9.780 | 1.6 |
|  | 0.78125 | 0.304687 | 2.370 | 1.1 |
|  | 0.390625 | 0.152343 | 0.960 | 1.0 |
|  | 0.195312 | 0.076171 | −0.090 | 0.9 |
|  | 0.097656 | 0.038085 | 2.880 | 1.1 |
| Simvastatin | 477 | 200 | 222.180 | 15.7 |
| 59-0328 | 238.5 | 100 | 304.100 | 21.2 |
|  | 119.25 | 50 | 189.430 | 13.5 |
|  | 59.625 | 25 | 180.640 | 13.0 |
|  | 29.8125 | 12.5 | 152.290 | 11.1 |
|  | 14.90625 | 6.25 | 104.640 | 7.9 |
|  | 7.453125 | 3.125 | 51.660 | 4.4 |
|  | 3.726562 | 1.5625 | 19.670 | 2.3 |
|  | 1.863281 | 0.78125 | 6.820 | 1.4 |
|  | 0.931640 | 0.390625 | 2.600 | 1.1 |
|  | 0.465820 | 0.195312 | 0.310 | 1.0 |
| Experiment 3 | | | | |
| Lovastatin | 247 | 100 | −32.660 | −0.002 |
| 59-0326 | 77.1875 | 31.25 | 166.770 | 6.118 |
|  | 24.12109 | 9.765625 | 148.030 | 5.543 |
|  | 7.537841 | 3.051757 | 103.260 | 4.169 |
|  | 2.355575 | 0.953674 | 35.300 | 2.083 |
|  | 0.736117 | 0.298023 | 10.860 | 1.333 |
|  | 0.230036 | 0.093132 | 3.210 | 1.099 |
|  | 0.071886 | 0.029103 | 1.550 | 1.048 |
|  | 0.022464 | 0.009094 | 2.720 | 1.083 |
|  | 0.007020 | 0.002842 | 1.050 | 1.032 |
|  | 0.002193 | 8.88178E | 0.620 | 1.019 |

|  | Sample Concentration | | % 59-0008 | Fold increase over negative |
|---|---|---|---|---|
| Experiment 3 | $\mu$M | $\mu$g/ml | Response | control |
| Fluvastatin | 235 | 100 | 60.3 | 4.14 |
| 59-0342 | 73.4375 | 31.25 | 122.53 | 7.38 |
|  | 22.94921 | 9.765625 | 103.7 | 6.4 |
|  | 7.171630 | 3.051757 | 22.66 | 2.18 |
|  | 2.241134 | 0.953674 | 2.3 | 1.12 |
|  | 0.700354 | 0.298023 | −3.26 | 0.83 |
|  | 0.218860 | 0.093132 | −2.11 | 0.89 |
|  | 0.068394 | 0.029103 | −5.18 | 0.73 |

-continued

| ABA Assay Results | | | |
|---|---|---|---|
| 0.021373 | 0.009094 | −3.84 | 0.8 |
| 0.006679 | 0.002842 | −3.26 | 0.83 |
| 0.002087 | 8.88178E | −0.19 | 0.99 |

The pravastatin that was tested did not exhibit a dose-dependent stimulatory response, but since this compound was extracted from formulated pravastatin, it is possible that insufficient and/or inactive compound was tested.

EXAMPLE 2

In vivo Calvarial Bone Growth Data

Lovastatin and simvastatin were assayed in vivo according to the procedure described previously (see "In vivo Assay of Effects of Compounds on Murine Calvarial Bone Growth", supra). Simvastatin provided a 1.5 fold increase in the number of osteoblasts.

In one experiment, vehicle control, bFGF and varying doses of simvastatin (59-0328) and lovastatin (designated 59-0326) were tested in the in vivo calvarial bone growth assay. The results are reported as a measurement of total bone area (and % increase in area over vehicle control), as shown below.

| Compound | Total Bone Area ($\mu m^2$) |
|---|---|
| Control | 167.7 |
| bFGF (12.5 $\mu$g/kg/day) | 242 (45%) |
| 59-0328 10 mg/kg/day | 245 (46%) |
| 59-0328 5 mg/kg/day | 202 (20%) |
| 59-0328 1 mg/kg/day | 172 (2%) |
| 59-0326 10 mg/kg/day | 239 (42%) |
| 59-0326 5 mg/kg/day | 235 (40%) |
| 59-0326 1 mg/kg/day | 237 (41%) |
| 59-0326 0.1 mg/kg/day | 162 (0%) |

Both simvastatin and lovastatin stimulated a dose-dependent increase in total bone area. At 10 mg/kg/day, the bone stimulatory effects of these statins were comparable to the bone growth effect observed when 12.5 $\mu$g/kg/day bFGF was tested in the same assay.

EXAMPLE 3

In vitro Bone Formation

Selected compounds and appropriate controls were assayed in vitro (ex vivo) for bone formation activity (described above in "Neonatal Mouse Calvaria Assay (in vitro)"). Histomorphometrical assessments of ex vivo calvaria were carried out using an OsteoMetrics bone morphometry measurement program, according to the manufacturer's instructions. Measurements were determined using either a 10- or 20-fold objective with a standard point counting eyepiece graticule.

New bone formation was determined (using a 10X objective) by measuring the new bone area formed in one field in 3 representative sections of each bone (4 bones per group). Each measurement was carried out ½ field distance from the end of the suture. Both total bone and old bone area were measured. Data were expressed as new bone area in mm².

Osteoblast numbers were determined by point counting. The number of osteoblast cells lining the bone surface on both sides of the bone were counted in one field using a 20X objective. Data were expressed as osteoblast numbers/mm of bone surface.

Lovastatin and simvastatin and control compounds/factors bFGF and BMP-2, and a vehicle control were tested in the in vitro bone formation assay and the calvaria were analyzed histomorphometrically, as described above. Several sets of experimental data are presented below, with % increase over vehicle control values indicated parenthetically.

| Compound | Osteoblast Number | |
|---|---|---|
| | 3 days Obs/field | 7 days Obs/field |
| Experiment 1 | | |
| Control | 97.25 | 92.7 |
| 59-0328 | 156 (63%) | 154 (68%) |
| BFGF | 179.25 (84%) | 168.7 (82%) |
| BMP-2 | 127 (31%) | 119 (28%) |
| Experiment 2 | | |
| Control | 90.7 | |
| 59-0328 | 154 (70%) | |
| Experiment 3 | | |
| Control | 84 | |
| 59-326 | 128 (152%) | |

| Compound | New Bone Area | |
|---|---|---|
| | 3 days (mm² × 10⁻³) | 7 days (mm² × 10⁻³) |
| Experiment 1 | | |
| Control | 4.8 | 7.8 |
| 59-0328 | 8.5 (77%) | 17.4 (123%) |
| BFGF | 5.7 (19%) | 18.1 (132%) |
| BMP2 | 8.4 (75%) | 18.7 (140%) |
| Experiment 2 | | |
| control | 4.0 | |
| 59-0328 | 15.4 (285%) | |
| Experiment 3 | | |
| Control | 4.5 | |
| 590-326 | 8.2 (182%) | |

These data show that lovastatin and simvastatin are as good as, or better than, BMP-2 and bFGF (two "gold standard" agents for bone growth; see Wozney J. *Molec Reprod Dev* (1992) 32:160–67; WO95/24211) for inducing bone formation. As shown in Example 2, in vivo calvarial studies using lovastatin and simvastatin have provided bone growth data consistent with these in vitro observations.

EXAMPLE 4

Effect on Resorption

The statins and controls were tested in an antiresorptive assay. Briefly, 15 day timed pregnant CD-1 female mice were injected with $^{45}$Ca (25 µCi/mouse). The calvaria from the 4 day old pups were dissected out and cut in half. The excised half calvaria were placed on metal grids (at the surface) in 1 ml of BGJ medium (Sigma) containing 0.1% BSA with glutamine and Pen/Strep added. The bones were incubated at 37° C. in a 5% humidified incubator for a period of 24 h, and then were transferred to wells containing 1 ml medium with factors added (IL-1, PTH, and/or test compounds). The treated bones were incubated under the above conditions for a further 72 h. After this incubation period, the bones were removed and placed into 20% TCA in a scintillation vial for 1.5 h, and then counted with scintillation fluid. An aliquot of medium (0.4 ml) was also counted. The results were expressed as % $^{45}$Ca release.

This assay may be modified by including test compounds/factors or control compounds/factors in the preincubation medium (i.e., during the first 24 h). Since most of the osteoclasts are formed in the calvaria following the preincubation period, compounds or factors that affect osteoclast formation may have a greater effect during the preincubation period.

In this assay, compound toxicity was indicated by obvious death of the cells in the periosteal region and within the marrow cavity of the bone organ cultures. These cells were characterized by pyknotic nuclei and vacuolated cytoplasm, characteristic of cell necrosis and distinct from apoptosis.

Using this assay, simvastatin was tested for its ability to inhibit IL-1 induced bone resorption. Briefly, IL-1 ($10^{-10}$ M) was added simultaneously with simvastatin (at 0.1, 1 or 10 µM) during a 72 h incubation period. Bone resorption was determined by measuring $^{45}$Ca release. IL-1, in the absence of simvastatin, increased $^{45}$Ca release about 2-fold over control calvaria incubated in the absence of IL-1 or simvastatin. Simvastatin at 0.1 or 1 µM concentration did not alter IL-1 induced $^{45}$Ca release. However, simvastatin at 10 µM concentration decreased IL-1 induced $^{45}$Ca release.

Histologic evaluation indicated toxicity at the 10 µM simvastatin. Previous studies have correlated toxicity with decreased $^{45}$Ca release.

These data suggest that simvastatin does not inhibit bone resorption at doses effective in the primary screening assay of Example 1. These results are contrary to reports by R. G. G. Russell and colleagues that mevastatin inhibits bone resorption in murine calvariae in vitro.

EXAMPLE 5

Systemic Administration of Statins in OVX Models

Lovastatin and simvastatin were analyzed in vivo using an acute OVX (prevention model) and/or chronic (treatment model) OVX model system, as described above under "Additional In Vivo Assays".

Lovastatin was examined in an acute OVX study. Briefly, 59-0326 was orally administered (35, 7, or 1.4 mg/kg/day; once per day for 35 days) immediately following ovariectomy. At the end of the study, the animals' blood and tissues samples were processed, and the following data were obtained.

pQCT analysis of samples removed from animals that received the 7 mg/kg/day dose showed a 20% increase in trabecular density and a 14% increase in cortical thickness. Histomorphometric analysis by two individuals showed an increase in trabecular bone volume of 110% (p<0.001) or 25% (p=0.0503) in the proximal tibia, and an increase of 23% (not significant) in the distal femur. The bone formation rate in the distal femur was increased 40% (p=0.052) in the 7 mg/kg/day animals.

Similarly, lovastatin was orally administered (0.1, 1, 5, 10, 20 or 40 mg/kg/day; once per day for 35 days) immediately following ovariectomy. Two individuals histomorphometrically analyzed samples removed from animals that received the 10 mg/kg/day dose. These analyses indicated an increase in trabecular bone volume of 38% (not significant) or 90% (p<0.02) in the proximal tibia. The bone formation rate in the proximal tibia was determined to have increased 74% (p=0.004) in animals that received a 10 mg/kg/day dose or 37% (p<0.008) in animals that received a 1 mg/kg/day dose. In samples from animals that received the 1 mg/kg/day dose, mineral apposition rate in the proximal tibia was increased 22%.

Simvastatin was also examined in a chronic OVX study. Briefly, simvastatin was orally administered (0.1, 1, 10, or 50 mg/kg/day; once per day for 10 weeks) to rats at 6 weeks post-ovariectomy. At the 10 mg/kg/day dose, a 114% (not significant) increase in the bone formation rate in the proximal tibia was measured. At the 50 mg/kg/day dose, an 86% (not significant) increase in the bone formation rate in the proximal tibia was measured.

EXAMPLE 6

Statin-Mediated Fracture Repair Effects of Test Compounds

Simvastatin was examined for effects on surgical defects in the rabbit radius. Healing of these defects may be assessed by X-ray, histology and biomechanical strength.

The test compound was weighed out in a microcentrifuge tube, and 50 $\mu$l of 1.5% sodium alginate solution was added as a carrier. This test sample was vortexed to wet all of the powder. The sample was sonicated for 20–30 min, and then vortexed again. Disks were created in the top of the microcentrifuge tube (by placing the tube lid or stopper-side down). The indent in the top of the stopper (i.e., lid) was used to form the disk (7.5 mm diameter). $CaCl_2$ solution (100 $\mu$l of 100 mM) was added to the sodium alginate/drug solution. The samples were allowed to sit for 5–10 min, and then the calcium-alginate disks were carefully removed. The disks were rinsed in a beaker filled with water to rinse off the excess calcium solution, and were saved in tubes using water as vehicle. All solutions and containers were sterile, and all procedures for preparations of disks were performed under a laminar flow hood under sterile conditions.

Bone healing was examined as follows. Briefly, six-month old male rabbits were obtained, and were divided into 4 treatment groups (n=3 animals/group). The treatment groups received either: 1) placebo; 2) test compound (5 mg/disk); 3) test compound (10 mg/disk); or 4) an autologous bone graft. Animals were anesthetized with rabbit cocktail (1 ml/1.5 kg intramuscularly), and the right forelimb was clipped, prepped and draped for aseptic surgery. Anesthesia was maintained using isofluorane delivered with a face mask. To create a 20 mm gap defect in the right mid-radius, an incision was made over the lateral aspect of the forearm, and an osteotomy was performed with an oscillating bone saw. The simvastatin or vehicle was applied to the defect and the defect was closed in layers. No external splinting was needed, as the radius is paired with the ulna, which functions to allow normal ambulation in the rabbit. Disks were cut on strips and inserted in the fracture to cover all the defect. Radiologic evaluation was performed at zero time and at 4 weeks.

Because the vehicle (placebo treatment group) prevented full healing in the control group, only X-ray results were obtained and analyzed. Accordingly, X-ray analysis 4 weeks after initiation of treatment showed callus formation at the bone treatment site in the treated (both doses), but not the placebo (vehicle or autologous bone graft) groups.

EXAMPLE 7

Stimulation of In Vitro Calvarial Bone Formation by Bisphosphonates

Various bisphosphonates were tested for their ability to stimulate calvarial bone formation in vitro in the assay described in Example 3 both alone and in combination with 59-0328 (simvastatin). The results were calculated as new bone area in $mm^2 \times 10^{-3}$, as above.

Dose response curves for ibandronate as a typical bisphosphonate showed a significant increase of bone formation at 10 $\mu$M ibandronate. These results are summarized below:

| | New Bone Area ($mm^2 \times 10^{-3}$) | | |
|---|---|---|---|
| | Experiment 1 | Experiment 2 | Experiment 3 |
| Control | 3.4 ± 0.5 | 3.5 ± 0.45 | 4.8 ± 0.6 |
| 0.01 $\mu$M | — | 3.5 ± 0.43 | — |
| 0.1 $\mu$M | — | 3.2 ± 0.56 | 6.2 ± 0.6 |
| 1 $\mu$M | — | 4.9 ± 1.2 | 7.5 ± 0.7 |
| 10 $\mu$M | 8.3 ± 0.7 | 7.2 ± 0.7 | 9.5 ± 2.4 |
| 100 $\mu$M | Toxic | Toxic | Toxic |
| 1000 $\mu$M | Toxic | Toxic | — |

Other bisphosphonates were tested as shown below; although alendronate, pamidronate and clodronate gave negligible effects under these conditions, risedronate showed significant increases in new bone area at 10 $\mu$M and 100 $\mu$M concentrations.

| | New Bone Area ($mm^2 \times 10^{-3}$) | | | |
|---|---|---|---|---|
| | Alendronate | Pamidronate | Clodronate | Risedronate |
| Control | 3.8 ± 0.5 | 5.0 ± 0.2 | 3.9 ± 0.5 | 3.8 ± 0.4 |
| 0.1 $\mu$M | 3.5 ± 0.3 | — | — | — |
| 1 $\mu$M | 5.2 ± 0.5 | — | — | — |
| 10 $\mu$M | 3.3 ± 0.6 | 6.0 ± 0.5 | 4.8 ± 1.3 | 8.5 ± 0.5 |
| 100 $\mu$M | Toxic | 5.8 ± 0.6 | 4.6 ± 0.6 | 7.3 ± 1.9 |
| 1000 $\mu$M | — | 5.2 ± 0.6 | 3.5 ± 0.5 | Toxic |

The effect of ibandronate together with simvastatin was also tested. The results are shown as follows:

| | New Bone Area ($mm^2 \times 10^{-4}$) | |
|---|---|---|
| | IBN (10 $\mu$M) | IBN (1 $\mu$M) |
| Control | 4.13 ± 0.035 | 3.77 ± 0.93 |
| Ibandronate (IBN) | 6.03 ± 1.56 | 3.95 ± 0.28 |
| 59-0328 (0.2 $\mu$M) | 6.83 ± 1.54 | 5.23 ± 0.89 |
| 59-0328 (0.1 $\mu$M) | 4.25 ± 0.59 | 5.1 ± 0.49 |
| IBN + 328 (0.2 $\mu$M) | 12.1 ± 1.7 | 7.6 ± 0.61 |
| IBN + 328 (0.1 $\mu$M) | 8.15 ± 0.77 | 7.82 ± 1.31 |

As shown, the combination of 59-0328 with ibandronate was superior to the result with either bisphosphonate alone.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method to enhance bone formation in a vertebrate animal which method comprises administering to a vertebrate subject in need of such treatment an amount of a compound of the formula:

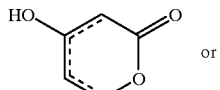  (1)

or

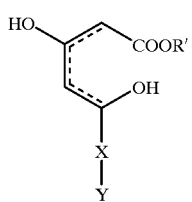  (2)

wherein X in each of formulas (1) and (2) represents an unsubstituted alkylene, alkenylene, or alkynylene linker of 2–6 C;

Y represents one or more carbocyclic or heterocyclic rings wherein, when Y comprises two or more rings, said rings may be fused; and R' represents a cation, H or a substituted or unsubstituted alkyl group of 1–6 C; and the dotted lines represent optional π bonds; and wherein said method further comprises administering at least one agent selected from the group consisting of
(a) a compound of the formula $Ar^1$—L—$Ar^2$  (10)

wherein each of $Ar^1$ and $Ar^2$ is independently substituted or unsubstituted phenyl, substituted or unsubstituted naphthyl, a substituted or unsubstituted aromatic system containing a 6-membered heterocycle or a substituted or unsubstituted aromatic system containing a 5-membered heterocycle;

(b) an estrogen or estrogen analog or mixture of estrogens and/or estrogen analogs; and (c) a bisphosphonate or bisphosphonate analog and/or mixture of bisphosphonates or bisphosphonate analogs;

wherein bone formation is effected.

2. The method of claim 1 wherein the composition comprises a compound of the formula

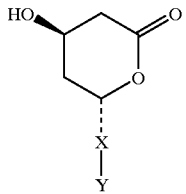  (3)

wherein X and Y are as defined in claim 1.

3. The method of claim 1 wherein X is selected from the group consisting of —$CH_2CH_2$—; —CH=CH—; and —C≡C—.

4. The method of claim 1 wherein Y is

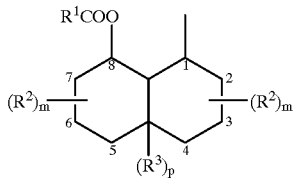  (4)

wherein $R^1$ is substituted or unsubstituted alkyl;

each $R^2$ is independently a noninterfering substituent;

$R^3$ is H, hydroxy, or alkoxy of;

each m is independently an integer of 0–6, wherein each $R^2$ may reside in any of positions 2–7; and p is 0 or 1, depending on the position of any π bonds indicated by the dotted lines.

5. The method of claim 4 wherein each m is independently 1 or 2 and wherein each $R^2$ resides in positions 2, 5 or 6.

6. The method of claim 5 wherein X is selected from the group consisting of —$CH_2CH_2$—; —CH=CH—; and —C≡C—.

7. The method of claim 6 wherein said composition comprises a compound wherein Y is of the formula

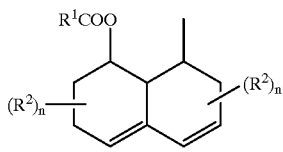  (4a)

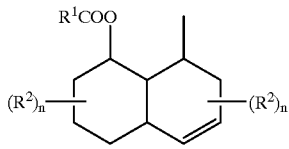  (4b)

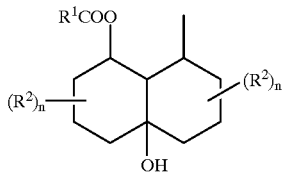  (4c)

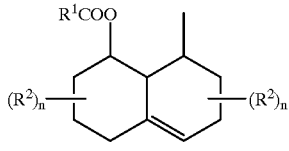  (4d)

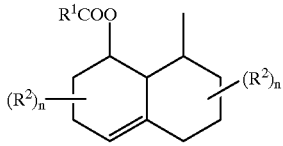  (4e)

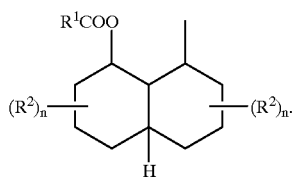
(4f)

8. The method of claim 7 wherein Y is of the formula

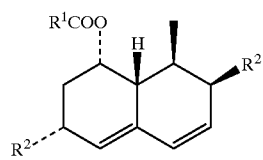
(4g)

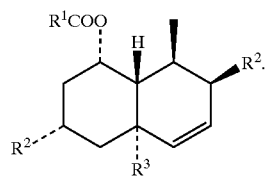
(4h)

9. The method of claim 1 wherein said composition comprises a compound wherein Y is

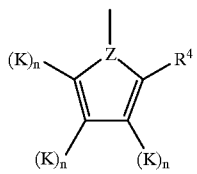
(5)

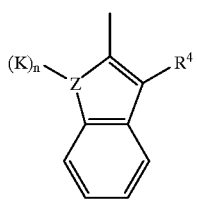
(6)

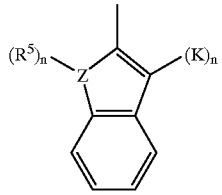
(7)

(8)

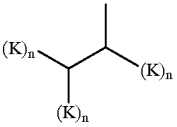
(9)

wherein each n is 0 or 1, but wherein at least one n in formula (5) and in formula (9) must be 1;

Z is CH or N, when n associated with its extra-ring substituent is 1 and is S or O when said n is 0;

each K comprises a substituted or unsubstituted aromatic or nonaromatic carbocyclic or heterocyclic ring system which may optionally be spaced from the linkage position shown in formulas (5)–(9) by a linker of 1–2 C;

each of $R^4$ and $R^5$ is independently H or linear or branched chain alkyl.

10. The method of claim 1 wherein said composition comprises a compound which is lovastatin, mevastatin, simvastatin or fluvastatin or a hydrolyzed form thereof or is pravastatin.

11. The method of claim 1 wherein said agent is a compound of the formula $$Ar^1—L—Ar^2 \qquad (10)$$

wherein each of $Ar^1$ and $Ar^2$ is independently a substituted or unsubstituted phenyl, substituted or unsubstituted naphthyl, substituted or unsubstituted aromatic system containing a 6-membered heterocycle or a substituted or unsubstituted aromatic system containing a 5-membered heterocycle; and L is a linker which spaces $Ar^1$ from $Ar^2$ at a distance of 1.5–15 Å; or a mixture of compounds of formula (10).

12. The method of claim 1 wherein said agent is an amount of an estrogen or estrogen analog or mixture of estrogens and/or estrogen analogs.

13. The method of claim 1 wherein said agent is an amount of a bisphosphonate or bisphosphonate analog or mixture of bisphosphonates and/or bisphosphonate analogs.

14. A method to enhance bone formation in a vertebrate animal which method comprises administering to a vertebrate subject in need of such treatment an amount of a compound of the formula:

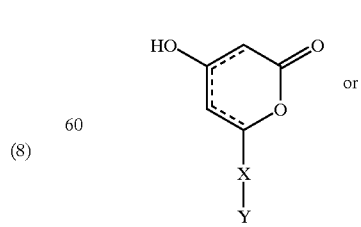
(1)

(2)

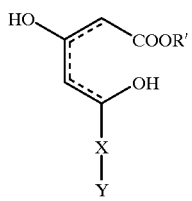

wherein X in each of formulas (1) and (2) represents a substituted or unsubstituted alkylene, alkenylene, or alkynylene linker of 2–6 C; and R' represents a cation, H or a substituted or unsubstituted alkyl group of 1–6 C; and the dotted lines represent optional π bonds, wherein Y is (4)

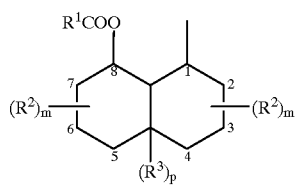

wherein $R^1$ is substituted or unsubstituted alkyl;

each $R^2$ is independently a noninterfering substituent;

$R^3$ is H, hydroxy, or alkoxy of 1–6 C;

each m is independently an integer of 0–6, wherein each $R^2$ may reside in any of positions 2–7; and p is 0 or 1, depending on the position of any π bonds indicated by the dotted lines, or wherein Y is (5)

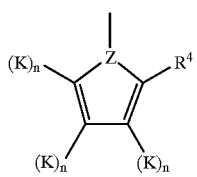

(6)

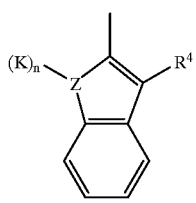

(7)

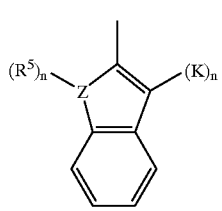

(8)

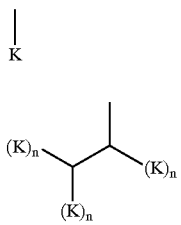

(9)

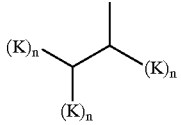

wherein each n is 0 or 1, but wherein at least one n in formula (5) and in formula (9) must be 1;

Z is CH or N, when n associated with its extra-ring substituent is 1 and is S or O when said n is 0;

each K comprises a substituted or unsubstituted aromatic or nonaromatic carbocyclic or heterocyclic ring system which may optionally be spaced from the linkage position shown in formulas (5)–(9) by a linker of 1–2 C;

each of $R^4$ and $R^5$ is independently H or linear or branched chain alkyl; and wherein said method further comprises administering at least one agent selected from the group consisting of (a) a compound of the formula $$Ar^1\text{—}L\text{—}Ar^2 \qquad (10)$$

wherein each of $Ar^1$ and $Ar^2$ is independently substituted or unsubstituted phenyl, substituted or unsubstituted naphthyl, a substituted or unsubstituted aromatic system containing a 6-membered heterocycle or a substituted or unsubstituted aromatic system containing a 5-membered heterocycle;

(b) an estrogen or estrogen analog or mixture of estrogens and/or estrogen analogs; and (c) a bisphosphonate or bisphosphonate analog and/or mixture of bisphosphonates or bisphosphonate analogs;

wherein bone formation is effected.

15. The method of claim 14 wherein each m is independently 1 or 2 and wherein each $R^2$ resides in positions 2, 5 or 6, or wherein X is selected from the group consisting of —CH₂CH₂—; —CH═CH—; and —C≡C—.

16. The method of claim 15 wherein Y is of the formula (4a)

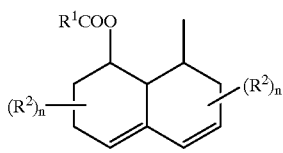

(4b)

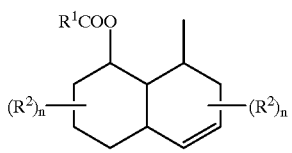

-continued

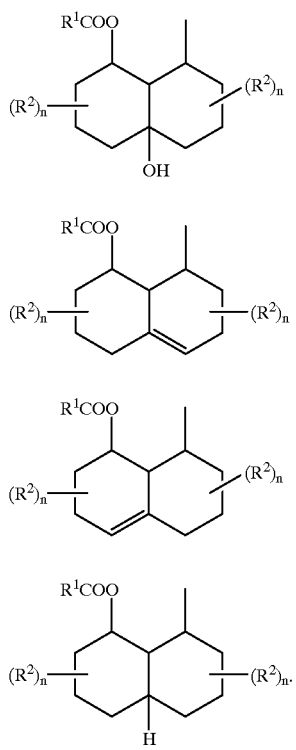

(4c)

(4d)

(4e)

(4f)

17. The method of claim 16 wherein Y is of the formula:

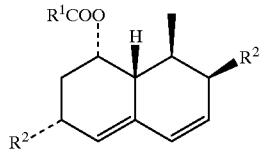

(4g)

-continued

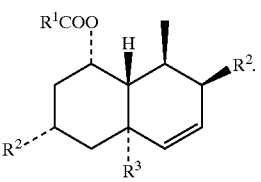

(4h)

18. The method of claim 14 wherein said agent is an amount of a compound of the formula $$Ar^1—L—Ar^2 \qquad (10)$$

wherein each of $Ar^1$ and $Ar^2$ is independently a substituted or unsubstituted phenyl, substituted or unsubstituted naphthyl, substituted or unsubstituted aromatic system containing a 6-membered heterocycle or a substituted or unsubstituted aromatic system containing a 5-membered heterocycle; and L is a linker which spaces $Ar^1$ from $Ar^2$ at a distance of 1.5–15 Å; or a mixture of compounds of formula (10).

19. The method of claim 14 wherein said agent is an amount of an estrogen or estrogen analog or mixture of estrogens and/or estrogen analogs.

20. The method of claim 14 wherein said agent is an amount of a bisphosphonate or bisphosphonate analog or mixture of bisphosphonates and/or bisphosphonate analogs.

* * * * *